United States Patent
MacKenzie et al.

(10) Patent No.: US 10,102,598 B2
(45) Date of Patent: Oct. 16, 2018

(54) DYNAMIC OPTIMAL CONNECTIVITY PATH

(71) Applicant: Passport Health Communications, Inc., Franklin, TN (US)

(72) Inventors: Gregory Scott MacKenzie, Nashville, TN (US); William Reed Ott, Goodlettsville, TN (US); Jason Harrison Wallis, Spring Hill, TN (US)

(73) Assignee: PASSPORT HEALTH COMMUNICATIONS, INC., Franklin, TN (US)

( * ) Notice: Subject to any disclaimer, the term of this patent is extended or adjusted under 35 U.S.C. 154(b) by 497 days.

(21) Appl. No.: 14/027,659

(22) Filed: Sep. 16, 2013

(65) Prior Publication Data

US 2015/0039328 A1  Feb. 5, 2015

Related U.S. Application Data

(60) Provisional application No. 61/859,994, filed on Jul. 30, 2013.

(51) Int. Cl.
*G06Q 50/00* (2012.01)
*G16H 10/00* (2018.01)
*G06Q 50/22* (2018.01)
*G06Q 20/02* (2012.01)

(52) U.S. Cl.
CPC .......... *G06Q 50/22* (2013.01); *G06Q 20/027* (2013.01); *G16H 10/00* (2018.01)

(58) Field of Classification Search
CPC ...... G06Q 50/22; G06Q 20/027; G16H 10/00; G16H 40/00
See application file for complete search history.

(56) References Cited

U.S. PATENT DOCUMENTS

| | | | | |
|---|---|---|---|---|
| 2010/0057934 A1* | 3/2010 | Ratica | ............. | G06F 9/505 709/240 |
| 2011/0029328 A1* | 2/2011 | Hasan | ............. | G06F 19/322 705/3 |
| 2013/0332193 A1* | 12/2013 | Kiselev et al. | ............. | 705/3 |
| 2014/0002851 A1* | 1/2014 | Smith et al. | ............. | 358/1.15 |

OTHER PUBLICATIONS

Helpton, Shane. "How to create a server failover solution." Posted May 16, 2013. Accessed at http://www.howto-expert.com/how-to-create-a-server-failover-solution/ on Jun. 28, 2015.*

* cited by examiner

*Primary Examiner* — Christopher L Gilligan
(74) *Attorney, Agent, or Firm* — Merchant & Gould

(57) ABSTRACT

Dynamically determining an optimum connectivity path is provided. Default paths to connectivity sources associated with a payer may be determined and ranked based on various metrics, such as availability, content, and cost. When a connection to a primary connectivity source is determined to be down or unresponsive, a request may automatically be routed to a next connectivity source, wherein the next connectivity source is determined to be a next highest ranking connectivity source based on the various metrics. Data associated with availability, content, cost, and other attributes may be collected, stored in a database, and utilized to rank connectivity sources. Accordingly, as new information about a payer or connectivity source is discovered, default paths and rankings of connectivity sources may change.

20 Claims, 3 Drawing Sheets

DYNAMIC OPTIMAL CONNECTIVITY PATH

CROSS-REFERENCE TO RELATED APPLICATIONS

The application claims priority to U.S. Provisional Patent Application No. 61/859,994 titled "Dynamic Optimal Connectivity Path" filed Jul. 30, 2013, the disclosure of which is hereby incorporated by reference in its entirety.

BACKGROUND

When a patient seeks healthcare services from a healthcare provider, the provider may collect various pieces of information from the patient prior to services being rendered. The provider may utilize the collecting information for a variety of preregistration processes, for example, insurance eligibility verification to determine if and what benefits a patient may be eligible to receive for healthcare services. In an insurance eligibility verification process, a request for benefit and eligibility information may be sent to one or more payers or other information sources; and accordingly, benefit and eligibility information may be returned to the provider in a response.

It is not uncommon that during this transaction for a connection to a payer or other information source to not be available (i.e., transactions are not being processed between the provider, or clearinghouse utilized by the provider, and the payer/information source). The provider (or clearinghouse) may have redundant connections to other information sources to which to send requests for benefit and eligibility information. Currently, when a connection to a payer or information source is determined to not be available, a user, such as an administrative user, may manually switch the traffic of connections (i.e., send requests for benefit and eligibility information) to another information source.

Oftentimes, an administrative user's productivity may be measured on throughput of registrations. When an unresponsive connection to a payer or other information source is encountered, the user's throughput, and thus, productivity, may be negatively affected through no fault of his/her own. When sending a request for information and waiting for a response to the request, the user may wish to experience as close to a real time transactional process as possible. It is with respect to these and other considerations that the present invention has been made.

SUMMARY

Embodiments of the present invention provide for dynamically determining an optimum connectivity path. According to embodiments, default paths to connectivity sources associated with a payer may be determined and may be ranked based on various metrics, such as availability, content, and cost. When a connection to a first or primary information source (herein referred to as a connectivity source) is determined to be unavailable or unresponsive, a request may automatically be routed to a next connectivity source, wherein the next connectivity source is determined to be a next highest ranking connectivity source based on the various metrics. Pings may be automatically sent to the unresponsive source to determine when the source is back up. Data associated with availability, content, cost, and other attributes may be collected, stored in a database, and utilized to rank connectivity sources. Accordingly, as new information about a payer or connectivity source is discovered, default paths and rankings of connectivity sources may change. Embodiments may provide for reliable and efficient transactions.

DETAILED DESCRIPTION

Figure 1:
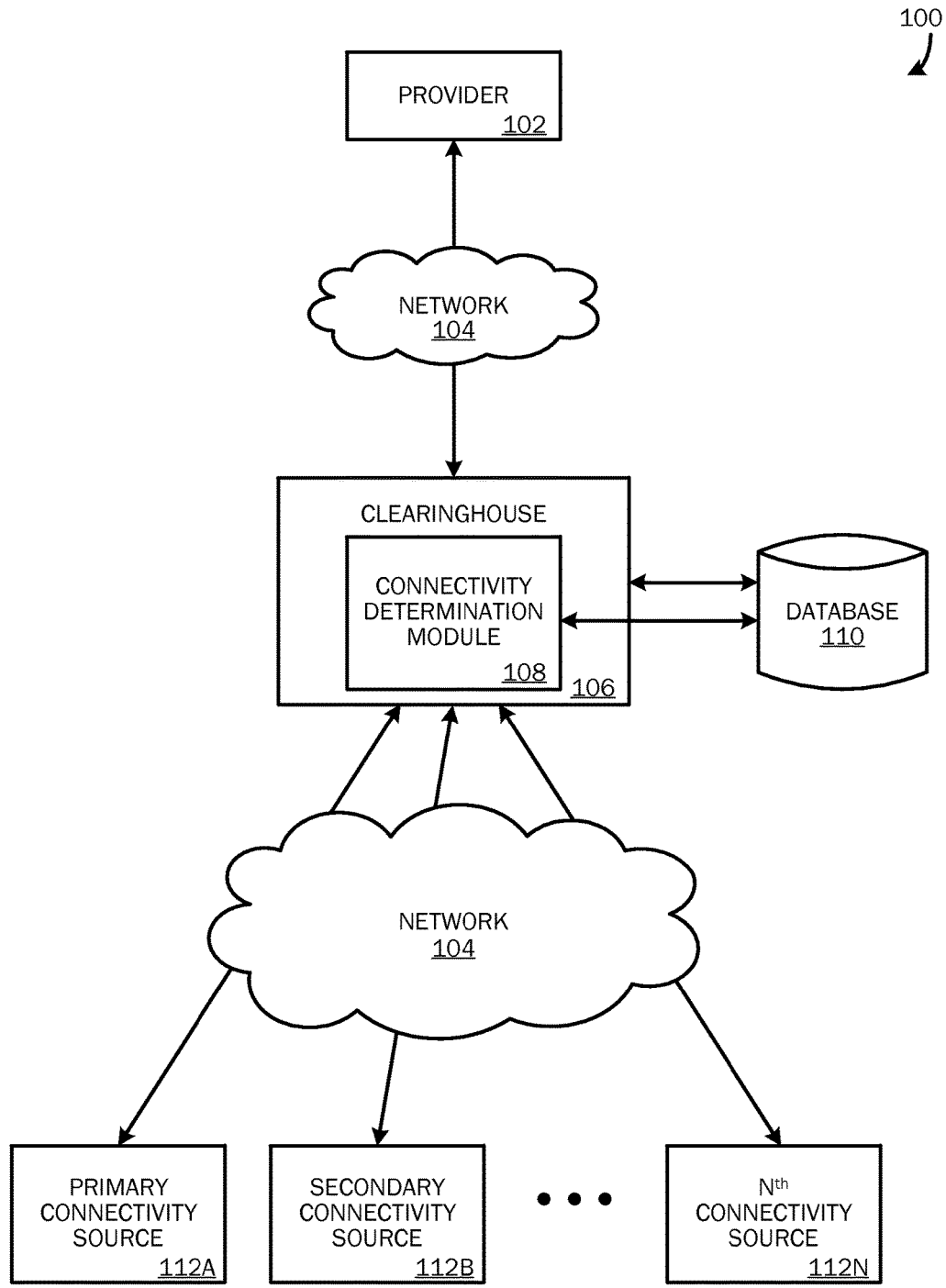
FIG. 1 is a simplified block diagram of a high-level system architecture with which embodiments of the invention may be implemented.

As briefly described above, embodiments of the present invention provide for dynamically determining an optimum connectivity path. When a provider wants to request information from an information source, such as requesting benefit and eligibility information from a payer, a request for the desired information may be sent to one or more payers or other information sources.

According to embodiments, a default path to one or more connectivity sources associated with a payer may be determined. The connectivity sources may be ranked based on various metrics, such as connection stability, pricing, and quality of data. When a connection to a first or primary connectivity source is determined to be unavailable or unresponsive, a determination may be made as to whether a second-ranked connectivity source (based on the various metrics) is available. If the secondary connectivity source is available, the request may be automatically rerouted to the secondary connectivity source; however, if the secondary connectivity source is unavailable, a determination may be made as to whether a third-ranked connectivity source (based on the various metrics) is available. The process may be repeated until a responsive connectivity source to which to send the request is found or if a responsive connectivity source is not available, the request may be put into a queue until a connectivity source is back up. Data associated with availability, content, cost, and other attributes may be collected, stored in a database, and utilized to rank connectivity sources. Accordingly, as new information about a payer or connectivity source is discovered, default paths and rankings of connectivity sources may change.

These embodiments may be combined, other embodiments may be utilized, and structural changes may be made without departing from the spirit or scope of the present invention. The following detailed description is therefore not to be taken in a limiting sense, and the scope of the present invention is defined by the appended claims and their equivalents. Referring now to the drawings, in which like numerals refer to like elements throughout the several figures, embodiments of the present invention and an exemplary operating environment will be described.

Referring now to FIG. 1, a simplified block diagram of a high-level system architecture 100 with which embodiments of the invention may be implemented is shown. Embodiments are described herein as relating to healthcare services transactions; however, as should be appreciated, embodiments are not limited to such and may be utilized in various types of operating environments. When an individual, such as a patient, seeks services from a provider 102, such as healthcare services from a healthcare provider, various pieces of information associated with the individual may be inputted into an information system associated with the provider 102. For example, if the provider 102 is a healthcare provider and the user is seeking healthcare services, the inputted information may include patient data such as demographics data (e.g., name, address, phone number(s), social security number, date of birth, gender, marital status, emergency contact information, employment status and details, student status and details, insurance information, etc.), admissions data, pre-registration data, coverage data, scheduling data, etc. If a guarantor of the individual's account is someone other than the individual, the information may also include data associated with the guarantor. The information may be used for various registration processes. For example, the information may be used for such processes as demographic information verification, insurance eligibility verification, pre-certification, financial clearance, etc.

A provider 102 may utilize a clearinghouse 106 to perform one or more of the above processes. The clearinghouse 106 may be operable to verify coverage and benefits data from a plurality of payers (i.e., insurance providers) or other trading partners, herein referred to as connectivity sources 112. According to an embodiment, the provider 102 (directly or via the clearinghouse 106) may request information from a payer or other connectivity source 112 to determine if a patient is eligible to receive benefits for healthcare services; and if the patient is eligible, the provider may request other benefit and eligibility information such as benefit amounts, co-insurance, co-pays, deductibles, exclusions, and limitations related to a specific procedure. The request for information may be sent as an eligibility request, for example, a 270 request or transaction. A payer may communicate eligibility benefit information associated with a subscriber or dependent in a response, for example, a 271 response or reply. Insurance eligibility verification may be performed in real-time or near real-time, which may allow the provider 102 to identify and collect any co-payments or other payments at the time of service. The provider 102 may send a request for insurance eligibility verification to a clearinghouse 106, and the clearinghouse 106 may send the request to a connectivity source 112 via a network 104, such as the Internet.

According to embodiments, the clearinghouse 106 may have redundant connections to payer data. That is, eligibility data may be available through different trading partners or connectivity sources 112. For example, the clearinghouse 106 may obtain eligibility data as a response to an eligibility request directly from a payer, or alternatively, the clearinghouse 106 may send a request for eligibility data from another clearinghouse or a trading partner.

Depending on various metrics, the clearinghouse 106 may rank connectivity sources 112 for each payer. The various metrics may include such metrics as connection stability, cost, quality of data, etc. For example, if a certain connectivity source 112 has a history of stable connections, offers good pricing, and provides good data, the connectivity source 112 may be highly ranked, and may be determined to be a primary connectivity source 112A to provide data for a particular payer. Alternatively, another connectivity source 112, which may have a history of less-stable connections, which may charge more for services, and/or which provides data that may be less comprehensive than data provided by the primary connectivity source 112A may be ranked lower, and be determined to be a secondary connectivity source 112B, a tertiary connectivity source, or lower (e.g., $N^{th}$ connectivity source 112N).

The clearinghouse 106 may comprise or connect to a database 110, which may be utilized to store information about connectivity sources 112. Information about the metrics and rankings of connectivity sources 112 may be stored in the database 110. Additionally, information about whether a connection to a connectivity source 112 is available (up), unavailable (down), or delayed (e.g., whether responses to requests are being received but are delayed, etc.) may be stored in the database 110. The database 110 may be updated in real-time or near real-time as transactions are being processed. For example, if a request for information is sent to a certain connectivity source 112 and a response is not received from the connectivity source 112, a determination may be made that the connectivity source 112 is unavailable. Accordingly, the connectivity source 112 may be marked as unavailable in the database 110.

According to embodiments, if a connectivity source 112 is marked as unavailable, pings may be sent to the connectivity source 112 until the connectivity source 112 is responsive. For example, messages may be transmitted over a network 104 to the connectivity source 112. When a connectivity source 112 is responsive (e.g., a reply from the connectivity source 112 is received), it may be determined to be back up or available. Accordingly, the connectivity source 112 may be marked as available in the database 110.

According to embodiments, the clearinghouse 106 may comprise or connect to a connectivity determination module 108 operable to determine an optimal connectivity path. The connectivity determination module 108 may utilize information stored in the database 110 to determine which connectivity source 112 to utilize to process a transaction. As mentioned above, connectivity sources 112 may be ranked according to various metrics. When a request is received from a provider 102 for information, the top-ranked or primary connectivity source 112A for the request may be identified, and the database 110 may be queried to verify whether the primary connectivity source 112A is available (i.e., if transactions are being successfully processed by the primary connectivity source 112A). If the primary connectivity source 112A is determined to be unavailable (i.e., transaction are not being successfully processed by the primary connectivity source 112A), the connectivity determination module 108 may query the database 110 to determine to which connectivity source 112 to send the request.

Figure 2:
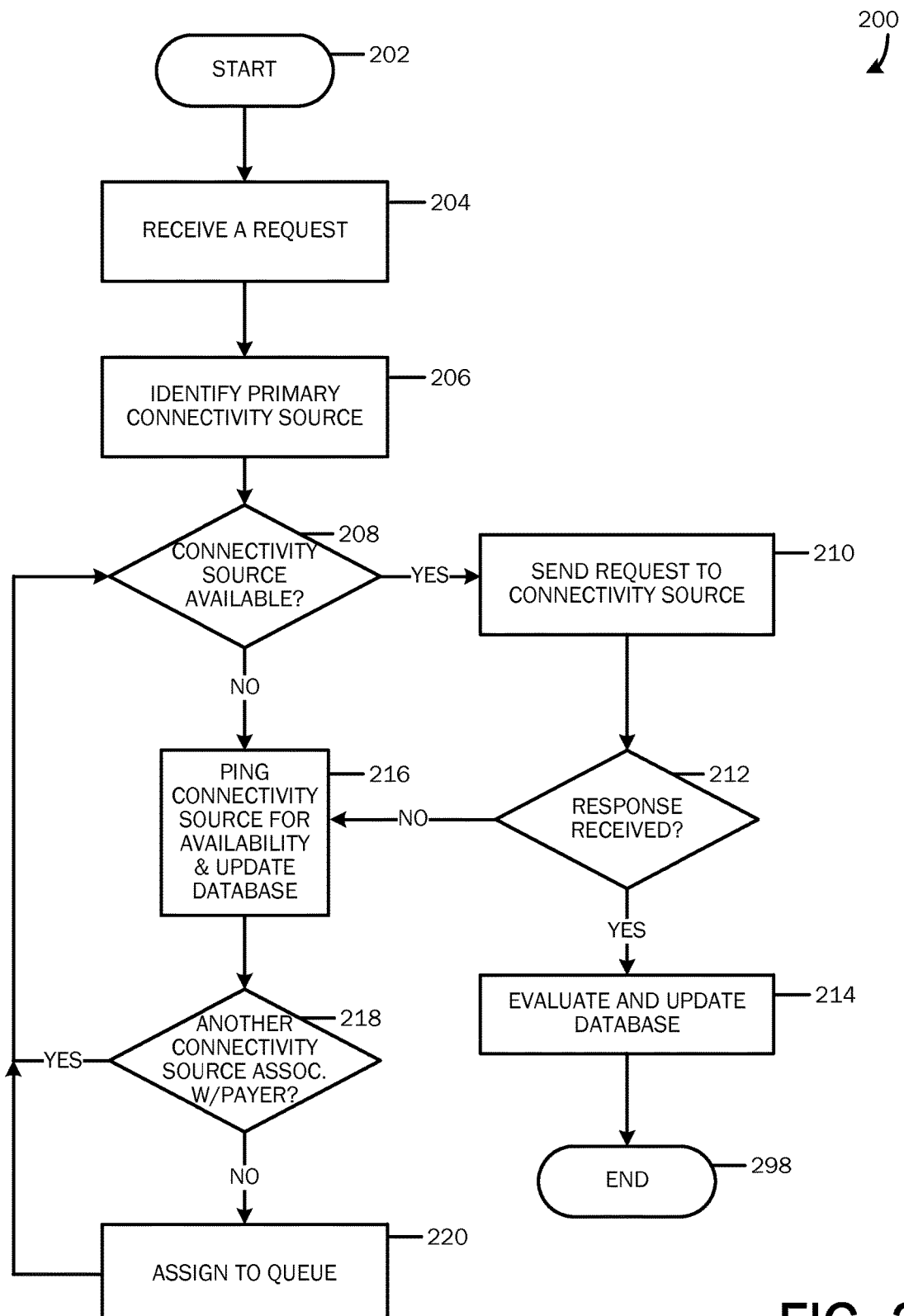
FIG. 2 is a flow chart of a method for dynamically determining an optimal connectivity path.

Having described a high-level system architecture 100, FIG. 2 is a flow chart showing one embodiment of a method 200 for providing a dynamic optimal connectivity path. The method 200 starts at OPERATION 202, and proceeds to OPERATION 204, where a request for information is received. For example, the request may be an insurance eligibility verification request for an individual seeking healthcare services from a healthcare provider 102. The request may be received by a clearinghouse 106, wherein the clearinghouse 106 may be operable to determine to which payer or other connectivity source 112 to transmit the request, and accordingly transmit the request to the determined payer or other connectivity source 112.

The method 200 may proceed to OPERATION 206, where a primary connectivity source 112A to which to send the request may be identified. Continuing with the example from above, the individual may claim to have insurance coverage from a certain payer. When the request is received, the database 110 may be queried to identify which connectivity source 112 may be the primary connectivity source 112A associated with the payer. As described above, connectivity sources 112 associated with a payer may be ranked according to various metrics, and the rankings may be stored in the database 110. In some cases, the primary connectivity source 112A may be the payer itself. In other cases, the primary connectivity source 112A may be another clearinghouse or other trading partner other than the payer.

When the primary connectivity source 112A is identified, the method 200 may proceed to DECISION OPERATION 208, where the connectivity determination module 108 may query the database 110 to determine if the primary connectivity source 112A is available (i.e., if transactions are being successfully processed by the primary connectivity source 112A). If the primary connectivity source 112A is determined to be available, the method 200 may proceed to OPERATION 210, where the request may be transmitted to the primary connectivity source 112A.

At DECISION OPERATION 212, a determination may be made as to whether a response from the primary connectivity source 112A is received. If a response is received, the method 200 may proceed to OPERATION 214, where the response may be evaluated, and metric data associated with the response may be stored in the database 110. For example, the response may be evaluated for such metrics as response time, quality of data, transaction cost, etc.

If a determination is made that the primary connectivity source 112A is not available at DECISION OPERATION 208 (i.e., transaction are not being successfully processed by the primary connectivity source 112A), or if a determination is made that a response is not received at DECISION OPERATION 212, the method 200 may proceed to OPERATION 216, where pings or messages may be sent to the primary connectivity source 112A until the primary connectivity source 112A is responsive and a reply is received. The status (e.g., available or unavailable) of the primary connectivity source 112A may be updated in the database 110.

The method 200 may proceed to DECISION OPERATION 218, where a determination may be made as to whether a next connectivity source 112 is associated with the payer, for example, a secondary connectivity source 11213, or the next highest-ranked connectivity source 112 in the database 110. As described above, connectivity sources 112 associated with a payer and rankings may be stored in the database 110. If a determination is made that there is another connectivity source 112 associated with the payer, the method may return to DECISION OPERATION 208 to determine whether the next highest-ranked connectivity source 112 is available. If the next highest-ranked connectivity source is unavailable, the method 200 may return to OPERATIONS 216-218. If the next highest-ranked connectivity source is available, the method 200 may return to OPERATIONS 210-218.

If another connectivity source 112 is not associated with the payer at DECISION OPERATION 218, the method may proceed to OPERATION 220, where the request may be assigned to a queue, wherein when a connectivity source 112 becomes available, the request may be processed (return to DECISION OPERATION 208). The method 200 may repeat OPERATIONS 208-212,216,218,220 until a response is received. As described above, when a response is received, the method 200 may proceed to OPERATION 214, where the response may be evaluated, and metric data associated with the response may be stored in the database 110. The method 200 may end at OPERATION 298.

Embodiments of the invention may be implemented via local and remote computing and data storage systems. Such memory storage and processing units may be implemented in a computing device, such as computing device 300 of FIG. 3. Any suitable combination of hardware, software, or firmware may be used to implement the memory storage and processing unit. For example, the memory storage and processing unit may be implemented with computing device 300 or any other computing devices 318, in combination with computing device 300, wherein functionality may be brought together over a network in a distributed computing environment, for example, an intranet or the Internet, to perform the functions as described herein. Such systems, devices, and processors (as described herein) are examples and other systems, devices, and processors may comprise the aforementioned memory storage and processing unit, consistent with embodiments of the invention.

Figure 3:
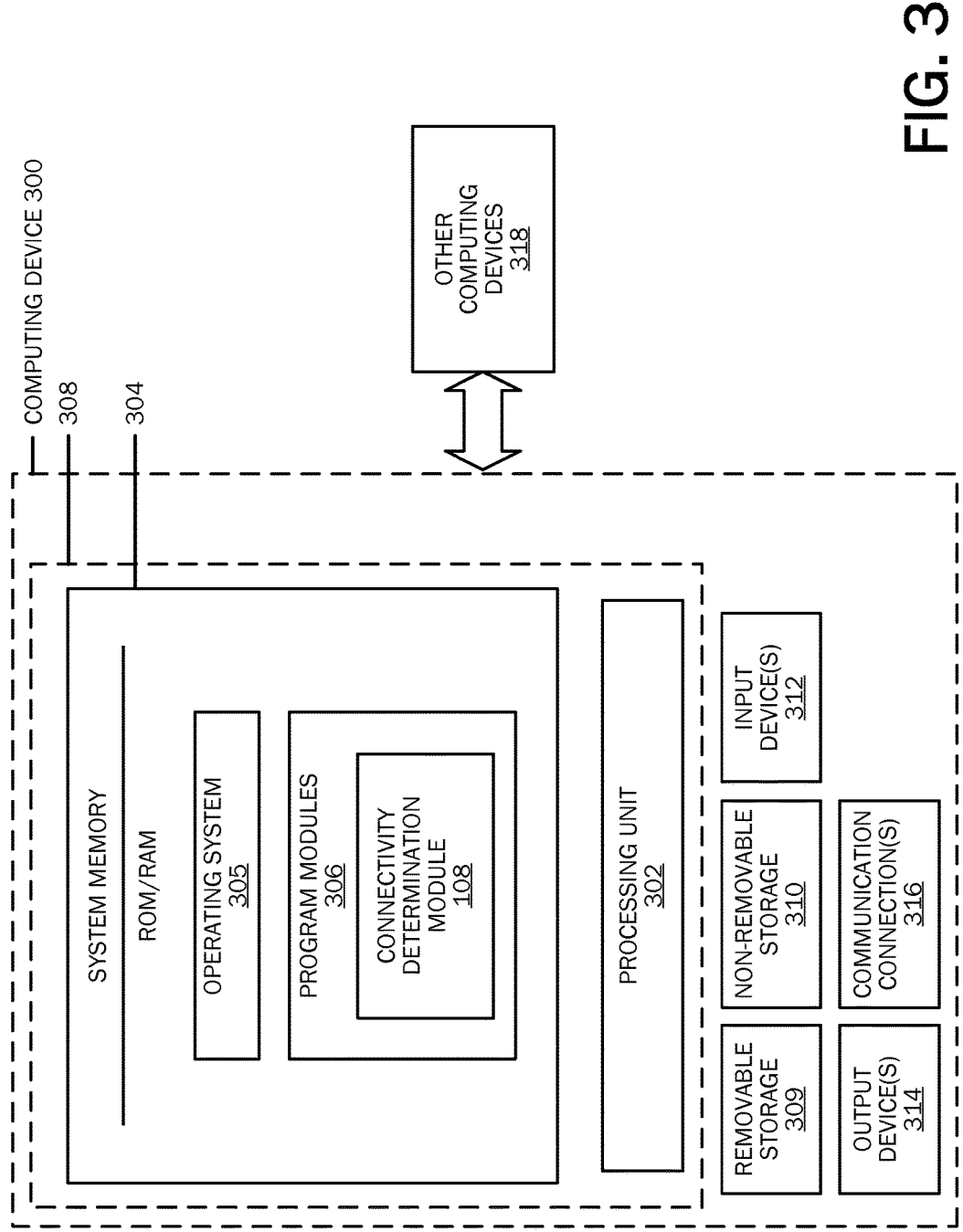
FIG. 3 is a simplified block diagram of a computing device with which embodiments of the present invention may be practiced.

With reference to FIG. 3, a system consistent with embodiments of the invention may include one or more computing devices, such as computing device 300. The computing device 300 may include at least one processing unit 302 and a system memory 304. The system memory 304 may comprise, but is not limited to, volatile (e.g. random access memory (RAM)), non-volatile (e.g. read-only memory (ROM)), flash memory, or any combination. System memory 304 may include operating system 305, one or more programming modules 306, and may include a connectivity determination module 108, wherein the connectivity determination module 108 is a software application having sufficient computer-executable instructions, which when executed, performs functionalities as described herein. Operating system 305, for example, may be suitable for controlling computing device 300's operation. Furthermore, embodiments of the invention may be practiced in conjunction with a graphics library, other operating systems, or any other application program and is not limited to any particular application or system. This basic configuration is illustrated in FIG. 3 by those components within a dashed line 308. Computing device 300 may also include one or more input device(s) 312 (keyboard, mouse, pen, touch input device, etc.) and one or more output device(s) 314 (e.g., display, speakers, a printer, etc.).

Although embodiments of the present invention have been described as being associated with data stored in memory and other storage mediums, data can also be stored on or read from other types of computer-readable media, such as secondary storage devices, like hard disks, floppy disks, or a CD-ROM, a carrier wave from the Internet, or other forms of RAM or ROM. Further, the disclosed methods' stages may be modified in any manner, including by reordering stages and/or inserting or deleting stages, without departing from the invention.

The computing device 300 may also include additional data storage devices (removable and/or non-removable) such as, for example, magnetic disks, optical disks, or tape. Such additional storage is illustrated in FIG. 3 by a removable storage 309 and a non-removable storage 310. Computing device 300 may also contain a communication connection 316 that may allow device 300 to communicate with other computing devices 318, such as over a network in a distributed computing environment, for example, an intranet or the Internet. Communication connection 316 is one example of communication media.

Program modules, such as the connectivity determination module 108, may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable user electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general purpose computer or in any other circuits or systems.

Embodiments of the invention, for example, may be implemented as a computer process (method), a computing system, or as an article of manufacture, such as a computer program product or computer readable media. The computer program product may be a computer storage media readable by a computer system and encoding a computer program of instructions for executing a computer process. Accordingly, the present invention may be embodied in hardware and/or in software (including firmware, resident software, microcode, etc.). In other words, embodiments of the present invention may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

Embodiments of the present invention, for example, are described above with reference to block diagrams and/or operational illustrations of methods, systems, and computer program products according to embodiments of the invention. For example, FIGS. 1-3 and the described functions taking place with respect to each illustration may be considered steps in a process routine performed by one or more local or distributed computing systems. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While the specification includes examples, the invention's scope is indicated by the following claims. Furthermore, while the specification has been described in language specific to structural features and/or methodological acts, the claims are not limited to the features or acts described above. Rather, the specific features and acts described above are disclosed as example for embodiments of the invention.

It will be apparent to those skilled in the art that various modifications or variations may be made in the present invention without departing from the scope or spirit of the invention. Other embodiments of the invention will be apparent to those skilled in the art from consideration of the specification and practice of the invention disclosed herein.

All rights including copyrights in the code included herein are vested in and the property of the Applicant. The Applicant retains and reserves all rights in the code included herein, and grants permission to reproduce the material only in connection with reproduction of the granted patent and for no other purpose.

We claim:

1. A method for dynamically determining an optimum connectivity path associated with a plurality of connectivity sources, the method comprising:
   using a clearinghouse as part of ranking the plurality of connectivity sources associated with a payer based on connection stability, pricing, and data quality that includes consideration of comprehensiveness of payer data provided by each of the plurality of connectivity sources, wherein the clearinghouse uses redundant connections to the payer data via the plurality of connectivity sources, wherein the clearinghouse ranks a connectivity source having a less-stable connection and which provides less comprehensive payer data lower than a connectivity source having a stable connection and which provides comprehensive payer data;
   storing the ranking of each of the plurality of connectivity sources in a database;
   updating the database in real-time or near real-time as transactions associated with one or more of the plurality of connectivity sources are being processed;
   receiving a request for information comprising benefit and eligibility information associated with healthcare services via the clearinghouse for the payer;
   using the ranking to identify a first connectivity source associated with the payer to which to send the request for information in order to provide the benefit and eligibility information associated with the payer;
   determining if the first connectivity source is currently available;
     sending the request for information to the first connectivity source when the first connectivity source is currently available in order to provide the benefit and eligibility information associated with the payer;
     sequentially identifying a second connectivity source associated with the payer according to the ranking that is currently available when the first connectivity source is currently unavailable; and
     sending the request for information to the second connectivity source when the second connectivity source is currently available in order to provide the benefit and eligibility information associated with the payer.

2. The method of claim 1, wherein identifying the first connectivity source associated with the payer to which to send the request for information comprises identifying a connectivity source designated as a primary connectivity source, wherein the primary connectivity source has a highest ranking amongst the plurality of connectivity sources.

3. The method of claim 2, wherein sequentially identifying the second connectivity source comprises identifying a next highest ranking connectivity source amongst the plurality of connectivity sources.

4. The method of claim 1, further comprising using the clearinghouse as part of ranking the plurality of connectivity sources according to metrics comprising connection stability information, cost information, and quality of data information.

5. The method of claim 1, further comprising storing, in the database, information about whether a connection to a connectivity source is available, information about whether a connection to a connectivity source is unavailable, and whether responses to requests are being received but are delayed, wherein determining if the first connectivity source is currently available comprises querying the database for availability information associated with the primary connectivity source.

6. The method of claim 5, further comprising:
determining if a response from the first connectivity source to which the request for information was sent is received;
evaluating the response and updating the database with metrics data associated with the first connectivity source when the response from the first connectivity source is determined to be received, wherein the evaluating of the response includes evaluating a response time, the data quality, and a transaction cost associated with the first connectivity source; and
when the response from the first connectivity source is determined not to be received:
updating the database with information that the first connectivity source is currently unavailable;
sequentially determining a next highest ranking connectivity source that is currently available; and
sending the request for information to the next highest ranking connectivity source when the next highest ranking connectivity source is determined to be currently available.

7. The method of claim 6, further comprising pinging the first connectivity source until a determination is made that the first connectivity source is currently available when the response from the first connectivity source is not received.

8. The method of claim 6, further comprising if the next highest ranking connectivity source that is currently available is not determined:
placing the request for information in a queue; and
when a connectivity source is determined to be currently available, sending the request for information to the currently available connectivity source.

9. A system for dynamically determining an optimum connectivity path associated with a plurality of connectivity sources, the system comprising:
a memory storage; and
a processor coupled to the memory storage, wherein the processor is operable to:
use a clearinghouse to rank the plurality of connectivity sources associated with a payer based on connection stability, pricing, and data quality that includes consideration of comprehensiveness of payer data provided by each of the plurality of connectivity sources, wherein the clearinghouse uses redundant connections to the payer data via the plurality of connectivity sources, wherein the clearinghouse ranks a connectivity source having a less-stable connection and which provides less comprehensive payer data lower than a connectivity source having a stable connection and which provides comprehensive payer data;
store the ranking of each of the plurality of connectivity sources in a database;
update the database in real-time or near real-time as transactions associated with one or more of the plurality of connectivity sources are being processed;
receive a request for information comprising benefit and eligibility information associated with healthcare services via the clearinghouse for the payer;
use the ranking as part of identify a first connectivity source associated with the payer to which to send the request for information including identifying a connectivity source designated as a primary connectivity source having a highest ranking amongst the plurality of connectivity sources in order to provide the benefit and eligibility information associated with the payer;
determine if the first connectivity source is currently available;
send the request for information to the first connectivity source when the first connectivity source is currently available in order to provide the benefit and eligibility information associated with the payer;
sequentially identify a second connectivity source associated with the payer according to the ranking that is currently available when the first connectivity source is currently unavailable, wherein the second connectivity source is a next highest ranking connectivity source amongst the plurality of connectivity sources; and
send the request for information to the second connectivity source when the second connectivity source is currently available in order to provide the benefit and eligibility information associated with the payer.

10. The system of claim 9, wherein the processor is operable to use the clearinghouse to rank the plurality of connectivity sources according to metrics comprising connection stability information, cost information, and quality of data information.

11. The system of claim 9, wherein the processor, in determining if the first connectivity source is currently available, is operable to query the database for availability information associated with the primary connectivity source.

12. The system of claim 9, wherein the processor is further operable to:
determine if a response from the first connectivity source to which the request for information was sent is received;
evaluate the response and update the database with metrics data associated with the connectivity source when the response from the first connectivity source is determined to be received; and
when the response from the first connectivity source is determined not to be received:
update the database with information that the first connectivity source is currently unavailable;
sequentially determine a next highest ranking connectivity source that is currently available; and
send the request for information to the next highest ranking connectivity source when the next highest ranking connectivity source is determined to be currently available.

13. The system of claim 12, wherein the processor is further operable to ping the first connectivity source until a determination is made that the first connectivity source is currently available.

14. The system of claim 12, wherein if the next highest ranking connectivity source that is currently available is not determined, the processor is further operable to:
place the request for information in a queue; and
when a connectivity source is determined to be currently available, send the request for information to the currently available connectivity source.

15. A non-transitory computer readable medium containing computer executable instructions which, when executed, perform a method of dynamically determining an optimum connectivity path associated with a plurality of connectivity sources comprising:

using a clearinghouse as part of ranking the plurality of connectivity sources associated with a payer based on connection stability, pricing, and data quality that includes consideration of comprehensiveness of payer data provided by each of the plurality of connectivity sources, wherein the clearinghouse uses redundant connections to the payer data via the plurality of connectivity sources, wherein the clearinghouse ranks a connectivity source having a less-stable connection and which provides less comprehensive payer data lower than a connectivity source having a stable connection and which provides comprehensive payer data;

storing the ranking of each of the plurality of connectivity sources in a database;

updating the database in real-time or near real-time as transactions associated with one or more of the plurality of connectivity sources are being processed;

receiving a request for information comprising benefit and eligibility information associated with healthcare services via the clearinghouse for the payer;

using the ranking to identify a first connectivity source associated with the payer to which to send the request for information including identifying a connectivity source designated as a primary connectivity source having a highest ranking amongst the plurality of connectivity sources in order to provide the benefit and eligibility information associated with the payer;

determining if the first connectivity source is currently available;

sending the request for information to the first connectivity source when the first connectivity source is currently available in order to provide the benefit and eligibility information associated with the payer;

sequentially identifying a second connectivity source associated with the payer according to the ranking that is currently available when the first connectivity source is currently unavailable, wherein the second connectivity source is a next highest ranking connectivity source amongst the plurality of connectivity sources; and sending the request for information to the second connectivity source when the second connectivity source is currently available in order to provide the benefit and eligibility information associated with the payer.

16. The computer readable medium of claim 15, wherein determining if the first connectivity source is currently available comprises querying the database for availability information associated with the primary connectivity source.

17. The computer readable medium of claim 15, further comprising using the clearinghouse as part of ranking the plurality of connectivity sources according to metrics comprising connection stability information, cost information, and quality of data information.

18. The computer readable medium of claim 15, further comprising:

determining if a response from the first connectivity source to which the request for information was sent is received;

evaluating the response and updating the database with metrics data associated with the first connectivity source when the response from the first connectivity source is determined to be received, wherein the evaluating of the response includes evaluating a response time, the data quality, and a transaction cost associated with the first connectivity source; and when the response from the first connectivity source is determined not to be received:
updating the database with information that the first connectivity source is currently unavailable;
sequentially determining a next highest ranking connectivity source that is currently available; and
sending the request for information to the next highest ranking connectivity source when the next highest ranking connectivity source is determined to be currently available.

19. The computer readable medium of claim 18, further comprising pinging the first connectivity source until a determination is made that the first connectivity source is currently available when the response from the first connectivity source is not received.

20. The computer readable medium of claim 18, further comprising if the next highest ranking connectivity source that is currently available is not determined:
placing the request for information in a queue; and
when a connectivity source is determined to be currently available, sending the request for information to the currently available connectivity source.

* * * * *